(12) United States Patent
Van Dijk

(10) Patent No.: US 12,089,981 B2
(45) Date of Patent: *Sep. 17, 2024

(54) INTERVENTIONAL SYSTEM

(71) Applicant: KONINKLIJKE PHILIPS N.V., Eindhoven (NL)

(72) Inventor: Erik Martinus Hubertus Petrus Van Dijk, Den Bosch (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 18/094,450

(22) Filed: Jan. 9, 2023

(65) Prior Publication Data

US 2023/0148987 A1 May 18, 2023

Related U.S. Application Data

(63) Continuation of application No. 14/648,382, filed as application No. PCT/IB2013/060701 on Dec. 6, 2013, now Pat. No. 11,576,644.

(Continued)

(51) Int. Cl.
*A61B 6/00* (2024.01)
*A61B 6/06* (2006.01)
(Continued)

(52) U.S. Cl.
CPC ............... *A61B 6/547* (2013.01); *A61B 6/06* (2013.01); *A61B 6/12* (2013.01); *A61B 6/4441* (2013.01);
(Continued)

(58) Field of Classification Search
None
See application file for complete search history.

(56) References Cited

U.S. PATENT DOCUMENTS 7,340,033 B2  3/2008  Mollus et al.
2002/0172328 A1  11/2002  Dekel et al.
(Continued)

FOREIGN PATENT DOCUMENTS

CN   101803952 A   8/2010
DE   102008062032 A1   7/2010
(Continued)

*Primary Examiner* — Patricia J Park

(57) ABSTRACT

The invention relates to an interventional system comprising an introduction element (4) like a catheter for being introduced into an object (9), for instance, a person. A moving unit (2) like a robot moves the introduction element within the object, wherein a tracking image generating unit (3) generates tracking images of the introduction element within the object and wherein a controller (8) controls the tracking image generating unit depending on movement parameters of the moving unit, which are indicative of the movement, such that the tracking images show the introduction element. This control can be performed very accurately based on the known real physical movement of the introduction element such that it is not necessary to, for instance, irradiate a relatively large area of the object for ensuring that the introduction element is really captured by the tracking images, thereby allowing for a reduced radiation dose applied to the object.

20 Claims, 2 Drawing Sheets

Related U.S. Application Data

(60) Provisional application No. 61/736,637, filed on Dec. 13, 2012.

(51) Int. Cl.
*A61B 6/12* (2006.01)
*A61B 6/50* (2024.01)
*A61B 34/20* (2016.01)
*A61B 34/30* (2016.01)
*A61B 90/00* (2016.01)

(52) U.S. Cl.
CPC .............. *A61B 6/481* (2013.01); *A61B 6/487* (2013.01); *A61B 6/54* (2013.01); *A61B 6/504* (2013.01); *A61B 2034/2065* (2016.02); *A61B 2034/301* (2016.02); *A61B 2090/376* (2016.02)

(56) References Cited

U.S. PATENT DOCUMENTS

| | | |
|---|---|---|
| 2004/0044279 A1 | 3/2004 | Lewin et al. |
| 2006/0258938 A1 | 2/2006 | Hoffman et al. |
| 2006/0247520 A1 | 11/2006 | McGee |
| 2008/0119725 A1 | 5/2008 | Lloyd |
| 2009/0182226 A1 | 7/2009 | Lee et al. |
| 2009/0234444 A1 | 9/2009 | Maschke et al. |
| 2010/0274120 A1 | 10/2010 | Heuscher et al. |
| 2012/0020547 A1* | 1/2012 | Zhao ............... G16H 30/40 382/153 |
| 2012/0179167 A1 | 7/2012 | Wenderow et al. |
| 2013/0343631 A1 | 12/2013 | Florent et al. |

FOREIGN PATENT DOCUMENTS

| | | |
|---|---|---|
| JP | 2008018172 A | 1/2008 |
| WO | 02091925 A1 | 11/2002 |
| WO | 2012077011 A1 | 6/2012 |
| WO | 2012123850 A1 | 9/2012 |

\* cited by examiner

INTERVENTIONAL SYSTEM

CROSS-REFERENCE TO RELATED APPLICATIONS

This application is a continuation application of U.S. application Ser. No. 14/648,382, filed on May 29, 2015, which is a U.S. National Phase application under 35 U.S.C. § 371 of International Application No. PCT/IB2013/060701 filed Dec. 6, 2013, which claims the benefit of U.S. Provisional Patent Application No. 61/736,637, filed on Dec. 13, 2012. These applications are hereby incorporated by reference herein.

FIELD OF THE INVENTION

The invention relates to an interventional system comprising an introduction element like a catheter for being introduced into an object, a moving unit like a robot for moving the introduction element within the object and a tracking image generating unit for generating tracking images of the introduction element within the object. The invention relates further to a corresponding interventional method and an interventional computer program. Moreover, the invention relates to a controller, a controlling method and a controlling computer program for controlling a radiation beam of the tracking image generating unit of the interventional system.

BACKGROUND OF THE INVENTION

WO 2012/123850 A1 discloses a medical imaging device for providing an image representation which is used for positioning an interventional device within a region of interest during an interventional procedure. The medical imaging device is adapted to acquire a pre-live anatomy image including the region of interest, to acquire a live anatomy image including the region of interest by using a live image acquisition device comprising an adjustable collimator and to identify a location of the interventional device within the live anatomy image. The medical imaging device is further adapted to adjust settings of the collimator based on the identified location of the interventional device, to subsequently acquire a further live anatomy image including the region of interest by using the live image acquisition device with the adjusted collimator and to provide the image representation by merging information from the live anatomy image into the pre-live anatomy image.

WO 2005/009243 A1 discloses an x-ray unit for generating images of a body, wherein the x-ray unit comprises an x-ray source, an automatically adjustable collimator for limiting, locally attenuating and/or filtering an x-ray beam, an x-ray detector and a data processing unit that is coupled to the collimator and the x-ray detector. The data processing unit is adapted to localize a region of interest inside the body on at least a first x-ray image of the body transmitted by the x-ray detector and to adjust the collimator such that subsequent x-ray images are concentrated on the region of interest.

If the x-ray unit is used for tracking a movement of a catheter tip within the body, i.e. if the region of interest is a moving region of interest defined by the moving catheter tip, and if this tracking is performed by acquiring a sequence of x-ray images, the x-ray source has to irradiate a relatively large region of the body, which corresponds to the largest distance the catheter tip can travel between consecutive x-ray images, in order to ensure that the catheter tip is really captured by the x-ray images and can therefore be tracked by using the x-ray unit. This relatively large irradiated region of the body results in a relatively large radiation dose applied to the body. Moreover, if the x-ray source is switched off for a short time and if the x-ray source is then switched on again, the location of the catheter tip is not known such that a relatively large part of the body has to be irradiated by the x-ray radiation, in order to find the moving catheter tip. Also this leads to a relatively large radiation dose.

SUMMARY OF THE INVENTION

It is an object of the present invention to provide an interventional system comprising an introduction element like a catheter for being introduced into an object, a moving unit like a robot for moving the introduction element within the object and a tracking image generating unit for generating tracking images of the introduction element within the object, which allows for generating tracking images which surely show the introduction element, even if the introduction element moves, with a reduced radiation dose. It is a further object of the present invention to provide a corresponding interventional method and interventional computer program, and to provide a controller, a controlling method and a controlling computer program for controlling a radiation beam of the tracking image generating unit of the interventional system.

In a first aspect of the present invention an interventional system is presented, wherein the interventional system comprises:

an introduction element for being introduced into an object,
a moving unit for moving the introduction element within the object,
a tracking image generating unit for generating tracking images of the introduction element within the object, wherein the tracking image generating unit comprises a radiation source for emitting a radiation beam for traversing the object, a radiation detector for detecting the radiation beam after having traversed the object and a controller for controlling the tracking image generating unit,
wherein the moving unit is adapted to provide movement parameters, which define a movement of the introduction element within the object, to the tracking image generating unit and wherein the controller is adapted to control the tracking image generating unit depending on the provided movement parameters such that the radiation beam traverses a region of the object that includes the introduction element.

Since the moving unit is adapted to provide movement parameters, which define a movement of the introduction element within the object, to the tracking image generating unit, the tracking image generating unit knows the real physical movement of the introduction element, which can be used by the controller for controlling the tracking image generating unit such that the radiation beam traverses a region of the object that includes the introduction element. This control of the radiation beam can be performed very accurately based on the known real physical movement of the introduction element such that it is not necessary to irradiate a relatively large area of the object for ensuring that the introduction element is really captured by the tracking images, thereby allowing for a reduced radiation dose applied to the object.

Preferentially, the movement parameters define a movement of the tip of the introduction element within the object, wherein the controller is adapted to control the tracking image generating unit depending on the provided movement parameters such that the radiation beam traverses a region of the object that includes the tip of the introduction element.

The introduction element is preferentially a catheter, a needle or another interventional instrument to be introduced into the object, which is preferentially a living object like a person or an animal. The moving unit is preferentially a robot for robotically moving the introduction element within the object, wherein this robotical movement can be performed automatically or by a user like a physician, who may control the moving unit via an input unit like a keyboard, a joystick, a touch screen, a mouse, et cetera. The tracking image generating unit is preferentially adapted to generate a sequence of tracking images showing the introduction element, while it moves within the object. Preferentially, the tracking image generating unit is adapted to generate x-ray images showing the introduction element within the object. The tracking image generating unit is, for instance, an x-ray C-arm unit.

The tracking image generating unit preferentially comprises a collimator for collimating the radiation beam, wherein the controller is adapted to control the collimator such that the radiation beam is collimated depending on the provided movement parameters such that the radiation beam traverses a region of the object that includes the introduction element. The controller may be adapted to control the collimator depending on a speed of the movement as defined by the movement parameters and/or a response time of the interventional system. In particular, the controller can be adapted to control the collimator depending on the speed of the movement as defined by the movement parameters and/or the response time of the interventional system such that a part of the radiation beam, which is in front of the introduction element with respect to a movement direction defined by the movement parameters, increases with increasing speed and/or with increasing response time.

Thus, the controller can be adapted to control the radiation beam by controlling the collimator of the tracking image generating unit. However, the controller can also be adapted to control other components of the tracking image generating unit for controlling the radiation beam like the radiation source and the radiation detector of the tracking image generating unit. For instance, the controller can be adapted to control the positions of these components for providing a desired direction of the radiation beam.

In a preferred embodiment the interventional system further comprises an identification unit for identifying the introduction element in the generated tracking images, wherein the controller is adapted to control the tracking image generating unit depending on the identification of the introduction element in the generated tracking images. Thus, not only the movement parameters may be used for controlling the tracking image generating unit, but also the identification of the introduction element in the generated tracking images. The identification of the introduction element in the generated tracking images is indicative of the real physical position of the introduction element within the object. Using this information regarding the real physical position of the introduction element within the object obtained from the tracking images together with the movement parameters provided by the moving unit for controlling the tracking image generating unit, in particular, the radiation beam, further improves the quality of tracking the introduction element by using the tracking images. For instance, the identification of the introduction element in the tracking images can be used to control the direction of the radiation beam, for example, the radiation beam can be controlled such that the introduction element, in particular, the tip of the introduction element, is centrally located within the tracking images, wherein the width of the radiation beam can be controlled depending on the movement parameters.

The identification unit is preferentially adapted to use known segmentation algorithms for segmenting the introduction element in the generated tracking images, in order to identify the introduction element.

The interventional system may further comprise a position determination unit for determining the position of the introduction element within the object based on the movement parameters, wherein the controller can be adapted to control the tracking image generating unit depending on the determined position of the introduction element. Moreover, the tracking image generating unit may comprise a collimator for collimating the radiation beam, wherein the position determination unit can be adapted to additionally determine an accuracy value being indicative of the accuracy of the determination of the position and wherein the controller can be adapted to control the collimator depending on the accuracy value. This allows controlling the tracking image generating unit during a switch off period, in which the tracking image generating unit temporally does not generate tracking images. If at the end of the switch off period the tracking image generating unit is switched on again, the generated tracking images immediately show the introduction element, even if the introduction element has been moved during the switch off period.

Preferentially, the controller is adapted to control the collimator such that the collimator has a narrower opening, if the accuracy value indicates a higher accuracy, and that the collimator has a wider opening, if the accuracy value indicates a lower accuracy. The accuracy value may be determined depending on, for instance, the speed of the movement defined by the movement parameters and/or depending on the total amount of movement defined by the movement parameters during a switch off period. The total amount of movement may be defined as being the total distance that the introduction element has travelled during the switch off period.

The interventional system may further comprise a) a position determination unit for determining the position of the introduction element within the object based on the movement parameters, b) an object image providing unit for providing an object image showing the object, and c) a display for displaying the object image and a representation of the introduction element at the determined position of the introduction element in the object image. The object image can be an overview image showing a larger part of the object. For instance, the object image can be a roadmap image showing a vessel tree of a person, wherein the introduction element may be moved within a vessel of the vessel tree. Since the position of the introduction element within the object is determined based on the movement parameters, wherein a representation of the introduction element at the determined position of the introduction element in the object image, for instance, in the roadmap image, is shown on the display, the position of the introduction element within the object can be shown on the display, even if currently a tracking image is not generated. For instance, the tip of an introduction element can be shown within a roadmap image, even if a tracking image is currently not generated.

The interventional system may also comprise a) an object image providing unit for providing an object image showing the object, b) an overlay image determining unit for determining an overlay image being an overlay of the object image and the target image, and c) a display for displaying the object image and the tracking image overlaid on each other. The object image can be, for instance, a roadmap image showing a vessel tree of a person. Since the tracking image shows the introduction element, by displaying the object image and the tracking image overlaid on each other, the position of the introduction element within the object can be shown to a user. Also in this embodiment the object image is preferentially an overview image showing a larger part of the object.

In a further aspect of the present invention a controller is presented, wherein the controller is adapted to control a radiation beam emitted by a radiation source of a tracking image generating unit depending on movement parameters provided by a moving unit for moving an introduction element within an object such that the radiation beam traverses a region of the object that includes the introduction element.

In another aspect of the present invention an interventional method is presented, wherein the interventional method comprises:
  moving an introduction element within an object by a moving unit,
  generating tracking images of the introduction element within the object by a tracking image generating unit, wherein a radiation beam for traversing the object is emitted by a radiation source of the tracking image generating unit and wherein the radiation beam is detected after having traversed the object by a radiation detector of the tracking image generating unit,
  wherein the moving unit provides movement parameters, which define a movement of the introduction element within the object, to the tracking image generating unit and wherein a controller controls the tracking image generating unit depending on the provided movement parameters such that the radiation beam traverses a region of the object that includes the introduction element.

In a further aspect of the present invention a controlling method for controlling a tracking image generating unit of an interventional system as defined in claim 1 is presented, wherein the controlling method comprises controlling the radiation beam depending on movement parameters provided by the moving unit of the interventional system such that the radiation beam traverses a region of an object that includes the introduction element.

In another aspect of the present invention an interventional computer program is presented, which comprises program code means for causing an interventional system as defined in claim 1 to carry out the steps of the interventional method as defined in claim 12, when the interventional computer program is run on a computer controlling the interventional system.

In a further aspect of the present invention a controlling computer program for controlling a radiation beam of a tracking image generating unit of an interventional system as defined in claim 1 is presented, wherein the controlling computer program comprises program code means for causing the controller of the tracking image generating unit to carry out the steps of the controlling method as defined in claim 13, when the controlling computer program is run on the controller.

It shall be understood that the interventional system of claim 1, the controller of claim 11, the interventional method of claim 12, the controlling method of claim 13, the interventional computer program of claim 14, and the controlling computer program of claim 15 have similar and/or identical preferred embodiments, in particular, as defined in the dependent claims.

It shall be understood that a preferred embodiment of the invention can also be any combination of the dependent claims or above embodiments with the respective independent claim.

These and other aspects of the invention will be apparent from and elucidated with reference to the embodiments described hereinafter.

BRIEF DESCRIPTION OF THE DRAWINGS

In the Following Drawings.

DETAILED DESCRIPTION OF EMBODIMENTS

Figure 1:
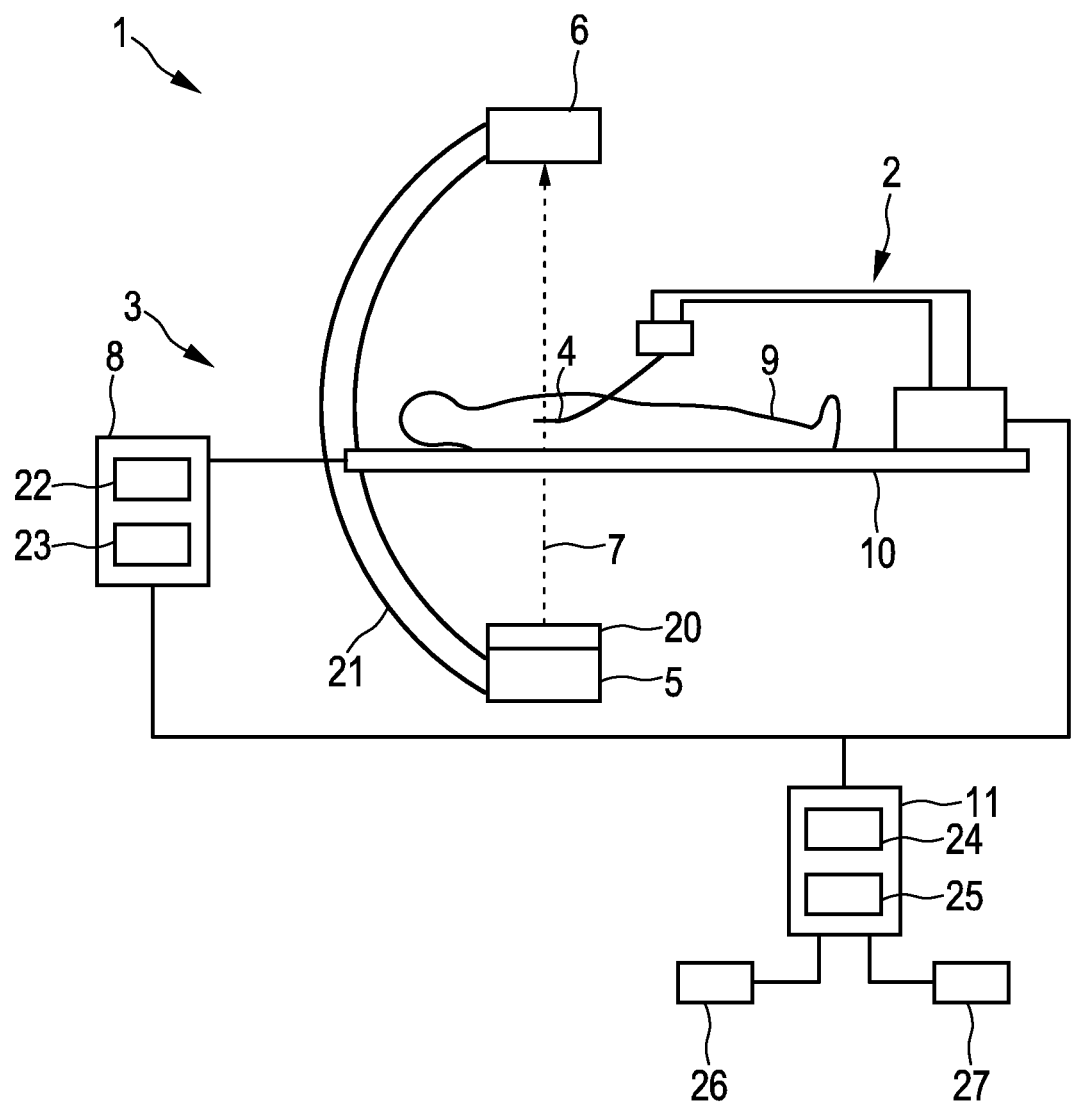
FIG. 1 shows schematically and exemplarily an embodiment of an interventional system.

FIG. 1 shows schematically and exemplarily an embodiment of an interventional system. In this embodiment, the interventional system is a catheter system 1 for introducing a catheter 4 into a person 9 lying on a support means like a patient table 10.

The catheter system 1 comprises a moving unit 2 for moving the catheter 4 within the person 9. In this embodiment, the moving unit 2 is a robotic unit for robotically moving the catheter 4 within the person 9. The robotic unit 2 is controlled by a user like a physician via an input unit 26. The input unit 26 may comprise a joystick, a keyboard, a mouse, a touchpad or another means for allowing the user to control the movement of the robotic unit 2.

The movement performed by the robotic unit 2 can be described by movement parameters, which may define a sequence of positions of the catheter 4, particularly of the tip of the catheter 4, within the person 9, and by corresponding time stamps such that for each position the respective time is known. The movement parameters are transferred from the robotic unit 2 to a tracking image generating unit 3.

The tracking image generating unit 3 is adapted to generate several tracking images, which correspond to different times and which show the catheter 4, particularly the tip of the catheter 4, at different positions during the movement. In this embodiment, the tracking image generating unit 3 is an x-ray C-arm system comprising an x-ray source 5 emitting an x-ray radiation beam 7 for traversing the person 9 with the catheter 4. The x-ray C-arm system 3 further comprises an x-ray detector 6 for detecting the radiation beam 7 after having traversed the person 9 with the catheter 4, and a controller 8 for controlling the radiation beam 7 and for generating x-ray projection images based on the radiation detected by the x-ray detector 6, wherein the generated x-ray projection images, i.e. the generated tracking images, show the catheter 4, particularly the tip of the catheter 4, within the person 9 at different positions during the movement, i.e. several tracking images are generated, which correspond to different times during the movement of the tip of the catheter 4 within the person 9. The images can be provided to a display 27 for showing the same.

The tracking image generating unit 3, i.e. the x-ray C-arm system 3, further comprises a collimator 20 for collimating the radiation beam 7, wherein the controller 8 is adapted to control the collimator 20 such that the radiation beam 7 is collimated depending on the provided movement parameters such that the radiation beam 7 traverses a region of the person 9 that includes the catheter 4, particularly the tip of the catheter 4. For instance, the controller 8 can be adapted to control the collimator 20 depending on the speed of the movement as defined by the movement parameters and/or a response time of the interventional system. In particular, the controller 8 can be adapted to control the collimator 20 depending on the speed of the movement as defined by the movement parameters and the response time of the interventional system 1 such that a part of the radiation beam 7, which is in front of the tip of the catheter 4 with respect to a movement direction defined by the movement parameters, increases with increasing speed and with increasing response time. The part of the radiation beam in front of the tip of the catheter 4 with respect to the movement direction defined by the movement parameters can be regarded as defining a safety margin. Since the movement parameters are used for controlling the safety margin, the safety margin can be smaller than a safety margin, which has to be used by a tracking image generating unit with a standard tight collimation technique as described in the above mentioned patent document WO 2005/009243 A1. The safety margin, i.e. in this example the part of the radiation beam in front of the tip of the catheter 4 with respect to the movement direction defined by the movement parameters, may be defined by following equation:

$$S > vt_r \qquad (1)$$

wherein S represents the safety margin in front of the tip of the catheter 4, v represents the speed in the movement direction, i.e. the corresponding speed set point of the robotic unit 2, and $t_r$ represents the response time of the interventional system.

The safety margin S and the speed v relate to quantities in the tracking images, i.e. S is a length in front of the tip of the catheter in the movement direction and v is the speed of the robotic unit as defined by the movement parameters with respect to an image reference frame defined by the tracking images, wherein the movement parameters, i.e. the velocity v defined by the movement parameters, have been transformed to correspond to the reference image frame. A transformation, which can be used for transforming the movement parameters to the image reference frame, is described further below.

The response time of the interventional system is preferentially defined as being the time between an action of motion of the introduction element within the person 9 and a control of the radiation beam in reaction of the action of motion. This response time depends on, for instance, the latency between the moving unit and the controller, the time needed by the collimator to react on inputs from the controller, et cetera.

An identification unit 23 can identify the catheter 4 in the generated tracking image and the controller 8 can control the radiation beam 7 such that the identified catheter 4 is centrally located or at another position within the tracking image. The identification unit 23 can use known segmentation algorithms for identifying the catheter 4 within the tracking images. The collimation, i.e. the width of the radiation beam 7, can be determined based on the movement parameters, for instance, based on the speed of movement as defined by the movement parameters as described above.

The interventional system can further comprise a position determination unit 22 for determining the position of the catheter 4, particularly of the tip of the catheter 4, within the person 9 based on the movement parameters, wherein the position determination unit 22 can be adapted to additionally determine an accuracy value being indicative of the accuracy of the determination of the position. This determined position and accuracy value is preferentially used for controlling the tracking image generating unit 3, if the tracking image generating unit 3 temporally does not generate tracking images, i.e. if the tracking image generating unit 3 is in a switch off period. This control is preferentially performed such that, if the generation of the tracking images is started again, the tracking images immediately show the tip of the catheter 4. Moreover, the control is preferentially performed such that the collimator 20 has a narrower opening, if the accuracy value indicates a higher accuracy, and that the collimator 20 has a wider opening, if the accuracy value indicates a lower accuracy. The position determination unit 22 is preferentially adapted to determine the accuracy value depending on the speed of the movement defined by the movement parameters during the switch off period and/or the total amount of movement defined by the movement parameters during the switch off period, wherein with increasing speed and/or increasing total amount of movement, respectively, the accuracy value decreases. The accuracy value can also be a function of the switch off time, wherein with increasing switch off time the accuracy value may decrease. The accuracy value may also depend on results from calibration steps performed for calibrating the interventional system. For instance, during a calibration procedure the accuracy of determining the position of the introduction element within the object based on the movement parameters can be determined by determining this position several times based on the same movement parameters, wherein the accuracy can be estimated depending on the resulting distribution of determined positions. For example, the accuracy value can be determined depending on the standard deviation of this distribution.

Thus, the interventional system allows estimating the location of the catheter 4, even if the x-ray source 5 is switched off. The location of the catheter 4 can be determined based on the movement as defined by the movement parameters and based on a known location of the catheter, from which the catheter 4 has been moved away. This known location can be a location, which has been determined by using a tracking image and by identifying the catheter 4 in the tracking image. If the x-ray source 5 is temporally switched off, this location of the catheter 4 determined by using the movement parameters can be used to control the components of the tracking image generating unit 3 defining the direction and shape of the radiation beam like the collimator 20 such that they follow the estimated location of the catheter 4. If then the x-ray source 5 is switched on again, the tracking image will capture the catheter 4 already very well, wherein the capturing of the catheter 4 can then be refined based on the generated tracking image.

In this embodiment the controller 8 comprises the position determination unit 22 and the identification unit 23. However, in another embodiment these units can also be arranged in another part of the interventional system 1, for instance, in another processing unit like the processing unit 11, which in this embodiment comprises an object image providing unit 24 for providing an object image showing the person 9. The object image providing unit 24 is adapted to provide an overview image preferentially including roadmap information showing vessels along which the catheter 4 can be moved within the person 9. The object image providing unit 24 is therefore preferentially adapted to provide a roadmap image. The roadmap image can be shown together with a representation of the tip of the catheter 4 at the position determined by the position determination unit 22 on the display 27, in order to allow a user like a physician to know the position of the tip of the catheter 4 within the person 9, even if the tracking image generating unit 3 does not provide actual tracking images, because, for instance, the radiation source 5 is switched off. The representation shown on the display 27 at the determined position of the tip of the catheter 4 can have the shape of a projection of the tip of the catheter 4 or it can have another shape. For instance, it can be circular, quadratically, et cetera. The catheter can therefore be blended in or artificially drawn into the provided object image.

The provided object image is preferentially an overview image that ensures that the user keeps a sense of the surrounding area. It can be a pre-acquired image, which may have been generated by the tracking image generating unit 3 or by another image generating device like a computed tomography imaging device, a magnetic resonance imaging device, et cetera. If the object image is a pre-acquired image, which has been generated by the tracking image generating unit 3, it may be an exposure or cine image or a fluo image. The exposure or cine image is generally generated by using a higher x-ray dose, after a contrast agent has been injected into the person, in order to generate a low noise image showing, for instance, a vessel tree. The fluo image is a noisier lower dose image. The exposure or cine image is preferred in comparison to the fluo image, because of the reduced noise.

The interventional system further comprises an overlay image determining unit 25 for determining an overlay image being an overlay of the object image and a target image. Since the catheter 4 is shown in the target image, by showing an overlay image being composed of the object image, which is preferentially an overview image showing the surrounding area, and the target image showing the catheter 4, the position of the catheter 4 in relation to the surrounding area within the person 9 can be shown to the user.

Figure 2:
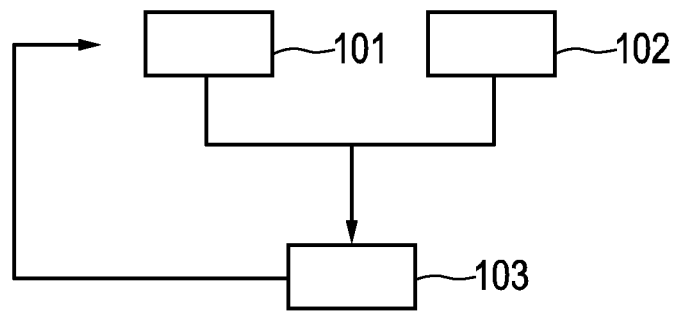
FIG. 2 shows a flowchart exemplarily illustrating an embodiment of an interventional method.

In the following an embodiment of an interventional method will exemplarily be described with reference to a flowchart shown in FIG. 2.

In step 101 an introduction element 4, which is introduced into an object 9, is moved by using a moving unit 2. In particular, a catheter 4 is moved within the person 9 by using the robotic unit 2 in accordance with an input into the robotic unit 2 provided by a user via the input unit 27.

In step 102 during the movement of the introduction element 4 within the object 9 tracking images of the introduction element 4 within the object 9 are generated by a tracking image generating unit 3, wherein a radiation beam 7 for traversing the object 9 is emitted by a radiation source 5 of the tracking image generating unit 3 and the radiation beam 7 is detected after having traversed the object 9 by a radiation detector 6 of the tracking image generating unit 3 for generating a tracking image.

In step 103 the radiation beam 7 is controlled by a controller 8, wherein the moving unit 2 provides movement parameters, which define a movement of the introduction element 4 within the object 9, to the tracking image generating unit 3 and wherein the controller 8 controls the radiation beam 7 depending on the provided movement parameters such that the radiation beam 7 traverses a region of the object 9 that includes the introduction element 4.

Preferentially, in step 103 the controller controls the radiation beam 7 also depending on the position of the introduction element 4 within the tracking image generated in step 102. Steps 101 to 103 are preferentially performed in a loop, wherein the controller 8 controls the radiation beam 7 such that the introduction element 4, in particular, the tip of the introduction element 4, is centrally located in the tracking images and such that the collimation, i.e. the width, of the radiation beam 7 is determined depending on the movement parameters received from the moving unit 2.

The procedure in accordance with step 103 can be regarded as defining a controlling method for controlling a radiation beam of a tracking image generating unit of an interventional system, wherein the controlling method comprises controlling the radiation beam depending on movement parameters provided by the moving unit of the interventional system such that the radiation beam traverses a region of an object that includes the introduction element.

Minimizing both staff and patient radiation dose for a given clinical procedure is a competitive issue in interventional x-ray procedures. In order to reduce these radiation doses, the above mentioned patent document WO 2005/009243 A1 discloses a tight collimation technique that automatically detects relevant regions of interest (ROIs) in technical images and that tries to limit the extent of the x-ray radiation beam as much as possible to only the ROI. By using this tight collimation technique, the dose area product can be reduced by reducing the irradiated area. The tight collimation technique uses image analysis algorithms for defining clinically relevant ROIs at any step of the interventional procedure. The image analysis algorithms can further be adapted to define safety margins around the clinical relevant ROIs, in order to take into account sudden movements of an interventional instrument like a catheter due to, for example, sudden movements performed by the physician.

If the tight collimation technique would be used, without considering the movement parameters provided by the moving unit 2, as described in the above mentioned patent document, the safety margin would need to be larger than the largest distance the introduction element can travel between consecutive frames, i.e. between consecutive tracking images generated by the tracking image generating unit 3. The corresponding region can be relatively large, for instance, it can cover an area being up to five times larger than the area of the clinically relevant ROI. This would lead to a relatively large radiation dose, even if the tight collimation technique is used. Furthermore, if the tight collimation technique would be used without considering the movement parameters provided by the moving unit 2 and if the x-ray source would be switched off momentarily, the interventional system would not know to which location the catheter has been moved and, thus, the interventional system would need to control the collimator such that its shutters are opened completely, in order to reacquire the introduction element upon reassuming the fluoroscopy process, i.e. upon resuming the generation of the several tracking images for tracking the introduction element within the person. The interventional system described above with reference to FIG. 1 is therefore adapted to use the movement information from the robotic unit 2 to aid in the tracking of the introduction element with the tight collimation.

The movement parameters, which can define translational information, can be transferred from the robotic unit 2 to the tracking image generating unit 3 via a wired or wireless data connection. Besides the movement parameters, also further information may be transferred from the robotic unit 2 to the tracking image generating unit 3 or to the processing unit 11 like the kind of the catheter moved by the moving unit 2. The kind of catheter can be indicative of the actual phase of the interventional procedure performed by the interventional system. The transferred movement parameters can include information about the shape and therewith the orientation of the catheter, i.e. the movement parameters can include information about the direction in which the catheter is pointing. This direction is the moving direction, in which the catheter is actually moved.

Since there may be some latency in the complete link chains, the catheter system is preferentially adapted to synchronize the image information provided by the tracking images and the movement parameters, i.e. the movement information, provided by the robotic unit 2. This synchronization is important, in order to allow the controller 8 to know, which image corresponds to which real physical movement defined by the movement parameters or to which real physical position of the catheter, in particular to which real physical position of the tip of the catheter, as defined by the movement parameters. Preferentially, the controller 8 uses times assigned to the sequence of real physical positions of the tip of the catheter 4 as defined by the movement parameters received from the robotic unit 2 and times, at which the generated tracking images showing the tip of the catheter 4 during the movement have been acquired, for synchronizing the real physical positions of the tip of the catheter 4 as defined by the movement parameters provided by the robotic unit 2 with the acquisition times of the generated tracking images. In this way it can be known, which sets of data belong to each other.

The robotic unit 2 can be, for instance, the CorPath 200 from the company Corindus, the Magalan system from the company Hansen Medical or another robotic unit, which can be used for moving an introduction element like a catheter within an object, wherein the respective robotic unit is adapted to provide the movement parameters to the tracking image generating unit 3. The robotic unit can be adapted to allow the user, for instance, a physician, to control the introduction element with, for instance, a joystick from behind a lead screen, in order to reduce the radiation dose received by the user.

The controller 8 can be adapted to convert the movement parameters obtained from the robotic unit 2 from a robot reference frame defined by the robotic unit 2 to an image reference frame defined by the tracking image generating unit 3. For performing this transformation corresponding transformation rules have to be determined, which relate the robot reference frame to the image reference frame. These transformation rules can be defined, for instance, by a calibration procedure, wherein positions and distances in the tracking images, i.e. in the image reference frame, are determined, while the corresponding positions and/or distances in the robot reference frame are known. This calibration can be performed pre-procedural, i.e. before the interventional procedure is performed, or during the interventional procedure, wherein in the latter case continuously catheter movements as input by the user into the robotic unit 2, i.e. corresponding positions and/or distances in the robot reference frame, are matched with corresponding changes visible in the tracking images. After the movement parameters have been transferred from the robot reference frame to the image reference frame, the above described determinations or calculations performed by the controller 8, which are performed for controlling the radiation beam depending on the movement parameters and depending on the identified introduction element identified in the tracking images, can be performed in the reference image frame.

The input from the robotic unit 2, i.e. the movement parameters, provided to the tracking image generating unit 3 can be used by the controller 8 for controlling the components defining the direction and the collimation of the radiation beam, if the radiation source 5 is switched off. This allows, for instance, the collimator, in particular one or several shutters of the collimator, to start moving in the right direction in accordance with the movement defined by the movement parameters, before the radiation source 5 is switched on again for acquiring a tracking image, thereby reducing the response time of the interventional system, which in turn can be used to reduce the safety margin in accordance with, for instance, equation (1).

The collimator 20 can be a standard collimator, in particular a standard symmetric collimator, as used in current x-ray C-arm systems. However, the collimator can also be a more complex collimator that allows for a more flexible control. For instance, the collimator may be a multileaf collimator, which may comprise multiple independently positionable leafs.

Although in above described embodiments the controller is adapted to control the tracking image generating unit such that the tip of the introduction element is centrally located within the tracking images, in other embodiments the tracking image generating unit can be controlled such that the tip of the introduction element is shown at another position within the tracking images. For instance, the tracking image generating unit can be controlled such that in front of the tip of the introduction element, i.e. in the direction of the movement of the introduction element in the image reference frame as defined by the transformed movement parameters that have been transformed to the image reference frame, the space within the tracking images is larger than behind the tip of the introduction element, i.e. larger than the space in the opposite direction, because it is more important for a user like a physician to have a visualization of the space, in which the tip of the introduction element is moved, than having a visualization of the space, from which the tip of the introduction element is moved away.

Although in the above described embodiments the tracking image generating unit is an x-ray C-arm system, in other embodiments the tracking image generating unit can also be another device for generating the tracking images, which comprises a radiation source for generating radiation traversing the object, a radiation detector for detecting the radiation, after it has traversed the object, and a controller for controlling the tracking image generating unit depending on movement parameters received from a moving unit for moving an introduction element within the object.

Although in above described embodiments the interventional system is a catheter system, in other embodiments the interventional system can also be another system adapted to perform an interventional procedure, wherein an interventional instrument is introduced into an object as the introduction element. For instance, instead of a catheter a needle can be used as the interventional instrument. In particular, the interventional system can be any interventional x-ray system.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Operations like the control of the radiation beam depending on the provided movement parameters, the determination of the position of the introduction element within the object based on the movement parameters, the determination of an accuracy value being indicative of the accuracy of the determination of the position of the introduction element, the identification of the introduction element in the generated tracking images, et cetera performed by one or several units or devices can be performed by any other number of units or devices. These operations and/or the control of the interventional system in accordance with the interventional method and/or the control of the radiation beam by the controller in accordance with the controlling method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to an interventional system comprising an introduction element like a catheter for being introduced into an object, for instance, a person. A moving unit like a robot moves the introduction element within the object, wherein a tracking image generating unit generates tracking images of the introduction element within the object and wherein a controller controls the tracking image generating unit depending on movement parameters of the moving unit, which are indicative of the movement, such that the tracking images show the introduction element. This control can be performed very accurately based on the known real physical movement of the introduction element such that it is not necessary to, for instance, irradiate a relatively large area of the object for ensuring that the introduction element is really captured by the tracking images, thereby allowing for a reduced radiation dose applied to the object.

The invention claimed is:

1. An interventional system comprising:
   a robot configured to move an interventional instrument within a patient anatomy from a first region to a second region that is different from the first region, the robot configured to provide movement parameters that define movement of the interventional instrument within the patient anatomy;
   an imaging system, external to the patient anatomy, configured to generate tracking images of the interventional instrument within the patient anatomy, the imaging system comprising:
   an imaging source configured to emit a beam for traversing the patient anatomy, and
   an imaging detector configured to detect the beam after having traversed the patient anatomy; and
   a controller configured to:
   receive the movement parameters from the robot and the tracking images from the imaging system,
   identify the interventional instrument in the tracking images, wherein the identified interventional instrument indicates a physical position of the interventional instrument within the patient anatomy at the second region, and
   control imaging parameters of the imaging system based on the physical position of the interventional instrument in the tracking images and the movement parameters received from the robot, so that the imaging system emits the beam to traverse the second region of the patient anatomy that includes the interventional instrument.

2. The interventional system as defined in claim 1, wherein the controller is further configured to control the imaging system to emit the beam to traverse the second region of the patient anatomy based on a response time of the interventional system.

3. The interventional system as defined in claim 1, wherein the controller is further configured to determine the physical position of the interventional instrument within the patient anatomy based on the movement parameters.

4. The interventional system as defined in claim 3, wherein the controller is further configured to:
   determine an accuracy value indicating accuracy of the determination of the physical position of the interventional instrument; and
   control the imaging system based on the accuracy value.

5. The interventional system as defined in claim 1, wherein the imaging system further comprises a collimator, and the controller is configured to control the collimator to collimate the beam based on a physical position that the robot moved the interventional instrument and the physical position of the interventional instrument in the tracking image, so that the beam traverses the second region of the patient anatomy including the interventional instrument.

6. The interventional system as defined in claim 5, wherein the controller is further configured to control the collimator to have a narrower opening when an accuracy value indicating accuracy of determination of the physical position of the interventional instrument indicates a higher accuracy, and to have a wider opening when the accuracy value indicates a lower accuracy.

7. The interventional system as defined in claim 1, wherein the controller is further configured to control a direction of the beam emitted by the imaging system based on the physical position of the identified interventional instrument in the tracking images and to control a width of the beam emitted by the imaging system based on a physical position that the robot moved the interventional instrument.

8. The interventional system as defined in claim 1, further comprising a position determination processor configured to:
   provide an object image showing the patient anatomy, and
   display the object image and a representation of the interventional instrument at a physical position of the interventional instrument in the object image.

9. The interventional system as defined in claim 1, wherein the movement parameters include information about one or more of: a shape, an orientation, a direction of movement, and a speed of the interventional instrument at a physical position that the robot moved the interventional instrument.

10. The interventional system as defined in claim 1, wherein:
    the robot defines a robot reference frame and is further configured to provide the movement parameters in the robot reference frame;
    the imaging system defines an image reference frame; and
    the controller is further configured to:
    transform a physical position that the robot moved the interventional instrument from the robot reference frame to the image reference frame, and
    control the imaging system based on the transformed physical position that the robot moved the interventional instrument.

11. A controller comprising:
a memory; and
a processor coupled to the memory and configured to:
receive movement parameters that define movement of an interventional instrument by a robot within a patient anatomy from a first region to a second region that is different than the first region,
receive tracking images generated by an imaging system that is external to the patient anatomy to track the interventional instrument within the patient anatomy,
identify, in the tracking images, a physical position of the interventional instrument within the patient anatomy at the second region, and
control imaging parameters of the imaging system, based on the physical position of the interventional instrument in the tracking images and the movement parameters received from the robot, so that the imaging system emits a beam that traverses the second region of the patient anatomy including the interventional instrument.

12. The controller as defined in claim 11, wherein the processor is further configured to control the imaging system to emit the beam to traverse the second region of the patient anatomy based on a response time of an interventional system comprising an interventional instrument.

13. The controller as defined in claim 11, wherein the processor is further configured to:
determine an accuracy value indicating accuracy of determination of the physical position of the interventional instrument; and
control the imaging system based on the accuracy value.

14. The controller as defined in claim 11, wherein the movement parameters include information about one or more of: a shape, an orientation, a direction of movement, and a speed of the interventional instrument at a physical position that the robot moved the interventional instrument.

15. The controller as defined in claim 1, wherein:
the robot defines a robot reference frame and is further configured to provide the movement parameters in the robot reference frame;
the imaging system defines an image reference frame; and
the processor is further configured to:
transform a physical position that the robot moved the interventional instrument from the robot reference frame to the image reference frame, and
control the imaging system based on the transformed physical position that the robot moved the interventional instrument.

16. A method comprising:
receiving movement parameters that define movement of an interventional instrument by a robot within a patient anatomy;
receiving tracking images generated by an imaging system that is external to the patient anatomy to track the interventional instrument within the patient anatomy;
identifying, in the tracking images, a physical position of the interventional instrument within the patient anatomy; and
controlling imaging parameters of the imaging system, based on the physical position of the interventional instrument in the tracking images and the movement parameters received from the robot, so that the imaging system emits a beam that traverses a second region of the patient anatomy including the interventional instrument.

17. The method as defined in claim 16, wherein the imaging system is configured to emit the beam to traverse the second region of the patient anatomy based on a response time of an interventional system comprising the interventional instrument.

18. The method as defined in claim 16, further comprising:
determining an accuracy value indicating accuracy of determination of the physical position of the interventional instrument; and
controlling the imaging system based on the accuracy value.

19. The method as defined in claim 16, wherein the movement parameters include information about one or more of: a shape, an orientation, a direction of movement, and a speed of the interventional instrument at a physical position that the robot moved the interventional instrument.

20. The method as defined in claim 16, wherein:
the robot defines a robot reference frame and is further configured to provide the movement parameters in the robot reference frame;
the imaging system defines an image reference frame; and
the method further comprises:
transforming a physical position that the robot moved the interventional instrument from the robot reference frame to the image reference frame, and
controlling the imaging system based on the transformed physical position that the robot moved the interventional instrument.

* * * * *